(12) United States Patent
Ni et al.

(10) Patent No.: US 11,014,076 B2
(45) Date of Patent: May 25, 2021

(54) CATALYST FOR SYNTHESIZING AROMATIC HYDROCARBONS AND PREPARATION METHOD THEREFOR

(71) Applicant: Dalian Institute of Chemical Physics, Chinese Academy of Sciences, Dalian (CN)

(72) Inventors: Youming Ni, Dalian (CN); Wenliang Zhu, Dalian (CN); Zhongmin Liu, Dalian (CN); Zhiyang Chen, Dalian (CN); Yong Liu, Dalian (CN); Hongchao Liu, Dalian (CN); Xiangang Ma, Dalian (CN); Shiping Liu, Dalian (CN)

(73) Assignee: Dalian Institute of Chemical Physics, Chinese Academy of Sciences, Dalian (CN)

(*) Notice: Subject to any disclaimer, the term of this patent is extended or adjusted under 35 U.S.C. 154(b) by 0 days.

(21) Appl. No.: 16/343,870

(22) PCT Filed: Aug. 22, 2017

(86) PCT No.: PCT/CN2017/098509
§ 371 (c)(1),
(2) Date: Apr. 22, 2019

(87) PCT Pub. No.: WO2018/076909
PCT Pub. Date: May 3, 2018

(65) Prior Publication Data
US 2019/0262811 A1    Aug. 29, 2019

(30) Foreign Application Priority Data

Oct. 24, 2016   (CN) .......................... 201610931965.1

(51) Int. Cl.
*B01J 29/06* (2006.01)
*B01J 29/40* (2006.01)
(Continued)

(52) U.S. Cl.
CPC ............. *B01J 29/405* (2013.01); *B01J 21/04* (2013.01); *B01J 21/066* (2013.01); *B01J 23/002* (2013.01); *B01J 23/005* (2013.01); *B01J 23/06* (2013.01); *B01J 23/26* (2013.01); *B01J 23/44* (2013.01); *B01J 23/72* (2013.01); *B01J 23/90* (2013.01); *B01J 29/08* (2013.01); *B01J 29/16* (2013.01); *B01J 29/185* (2013.01); *B01J 29/22* (2013.01); *B01J 29/24* (2013.01); *B01J 29/26* (2013.01); *B01J 29/40* (2013.01); *B01J 29/44* (2013.01); *B01J 29/46* (2013.01); *B01J 29/48* (2013.01); *B01J 29/7049* (2013.01); *B01J 29/7057* (2013.01); *B01J 29/7069* (2013.01); *B01J 29/7088* (2013.01); *B01J 29/72* (2013.01); *B01J 29/7215* (2013.01); *B01J 29/7238* (2013.01); *B01J 29/7415* (2013.01); *B01J 29/7438* (2013.01); *B01J 29/7615* (2013.01);
(Continued)

(58) Field of Classification Search
CPC ... B01J 29/22; B01J 29/24; B01J 29/26; B01J 29/08; B01J 29/16; B01J 29/46; B01J 29/48; B01J 29/44; B01J 29/405; B01J 29/18; B01J 29/185; B01J 29/7615; B01J 29/7638; B01J 29/7815; B01J 29/7838; B01J 29/7876; B01J 29/7049; B01J 29/7069; B01J 29/7057; B01J 29/72; B01J 29/7215; B01J 29/7088; B01J 29/7238; B01J 29/7415; B01J 29/7438; B01J 37/04; B01J 37/0063; B01J 37/031; B01J 37/03; B01J 23/002; B01J 23/44; B01J 23/90; B01J 23/005; B01J 23/06; B01J 23/72; B01J 35/023; B01J 35/0006; B01J 21/04; B01J 21/066; B01J 2229/20; B01J 2229/37; B01J 2523/17; B01J 2523/824; B01J 2523/27; B01J 2523/31; B01J 2523/67; B01J 2523/48; Y02P 20/52; C07C 2529/40; C07C 2521/04; C07C 2523/06
USPC ........ 502/63, 64, 66, 69, 71, 73, 74, 77, 78, 502/79, 326, 327, 328, 329
See application file for complete search history.

(56) References Cited

U.S. PATENT DOCUMENTS 4,096,163 A     6/1978  Chang et al.
4,487,984 A *  12/1984  Imai ....................... C07C 2/862
                                                                585/454
(Continued)

FOREIGN PATENT DOCUMENTS

CN          1057476 A       1/1992
CN          1080313 A       1/1994
(Continued)

OTHER PUBLICATIONS

Erena et al., "Study of Physical Mixtures of Cr2O3—ZnO and ZSM-5 Catalysts for the Transformation of Syngas into Liquid Hydrocarbons", Ind. Eng. Chem. Res. 37, pp. 1211-1219, 1998.*

(Continued)

*Primary Examiner* — Elizabeth D Wood
(74) *Attorney, Agent, or Firm* — Edwin A. Sisson, Attorney at Law, LLC; Jeffrey J. Banyas

(57) ABSTRACT

A catalyst for synthesizing aromatic hydrocarbons, a preparation method thereof and a method for synthesizing aromatic hydrocarbons by using the catalyst. The catalyst comprises acidic molecular sieve particles and zinc-aluminum composite oxide particles. The catalyst has relatively high selectivity to aromatic hydrocarbons, particularly BTX, stable performance, and a long single-pass life.

12 Claims, No Drawings

(51) Int. Cl.

| | | |
|---|---|---|
| *B01J 23/00* | (2006.01) | |
| *B01J 29/44* | (2006.01) | |
| *B01J 29/46* | (2006.01) | |
| *B01J 29/48* | (2006.01) | |
| *B01J 29/90* | (2006.01) | |
| *B01J 37/03* | (2006.01) | |
| *B01J 37/04* | (2006.01) | |
| *B01J 38/12* | (2006.01) | |
| *C01B 39/02* | (2006.01) | |
| *C07C 1/04* | (2006.01) | |
| *B01J 38/14* | (2006.01) | |
| *B01J 21/06* | (2006.01) | |
| *B01J 21/04* | (2006.01) | |
| *B01J 35/02* | (2006.01) | |
| *B01J 23/72* | (2006.01) | |
| *B01J 23/26* | (2006.01) | |
| *B01J 37/00* | (2006.01) | |
| *B01J 35/00* | (2006.01) | |
| *B01J 38/02* | (2006.01) | |
| *B01J 23/44* | (2006.01) | |
| *B01J 23/06* | (2006.01) | |
| *B01J 23/90* | (2006.01) | |
| *B01J 29/76* | (2006.01) | |
| *B01J 29/08* | (2006.01) | |
| *B01J 29/22* | (2006.01) | |
| *B01J 29/16* | (2006.01) | |
| *B01J 29/18* | (2006.01) | |
| *B01J 29/26* | (2006.01) | |
| *B01J 29/24* | (2006.01) | |
| *B01J 29/70* | (2006.01) | |
| *B01J 29/78* | (2006.01) | |
| *B01J 29/74* | (2006.01) | |
| *B01J 29/72* | (2006.01) | |

(52) U.S. Cl.
CPC ....... *B01J 29/7638* (2013.01); *B01J 29/7815* (2013.01); *B01J 29/7838* (2013.01); *B01J 29/7876* (2013.01); *B01J 29/90* (2013.01); *B01J 35/0006* (2013.01); *B01J 35/023* (2013.01); *B01J 37/0063* (2013.01); *B01J 37/03* (2013.01); *B01J 37/031* (2013.01); *B01J 37/04* (2013.01); *B01J 38/02* (2013.01); *B01J 38/12* (2013.01); *B01J 38/14* (2013.01); *C01B 39/026* (2013.01); *C07C 1/045* (2013.01); *C07C 1/0435* (2013.01); *C07C 1/0445* (2013.01); *B01J 29/18* (2013.01); *B01J 2229/20* (2013.01); *B01J 2229/37* (2013.01); *B01J 2523/17* (2013.01); *B01J 2523/27* (2013.01); *B01J 2523/31* (2013.01); *B01J 2523/48* (2013.01); *B01J 2523/67* (2013.01); *B01J 2523/824* (2013.01); *C07C 2521/04* (2013.01); *C07C 2523/06* (2013.01); *C07C 2529/40* (2013.01); *Y02P 20/52* (2015.11)

(56) References Cited

U.S. PATENT DOCUMENTS

| | | | | |
|---|---|---|---|---|
| 4,665,238 | A * | 5/1987 | Imai | C07C 2/862 502/78 |
| 4,975,402 | A * | 12/1990 | Le Van Mao | B01J 29/40 502/68 |
| 5,135,898 | A * | 8/1992 | Le Van Mao | B01J 23/08 502/61 |
| 6,459,006 | B1 * | 10/2002 | Ou | B01J 23/002 585/454 |
| 2010/0041932 | A1 * | 2/2010 | Dodwell | B01J 29/06 585/469 |
| 2013/0008827 | A1 * | 1/2013 | Nagayasu | B01J 29/7461 208/64 |
| 2014/0350317 | A1 * | 11/2014 | Blommel | C10G 3/50 585/322 |
| 2015/0080621 | A1 * | 3/2015 | Powell | C01B 3/32 585/240 |

FOREIGN PATENT DOCUMENTS

| | | |
|---|---|---|
| CN | 101422743 A | 5/2009 |
| CN | 102382678 A | 3/2012 |
| CN | 103100415 A | 5/2013 |
| CN | 104549475 A | 4/2015 |
| CN | 106281400 A | 1/2017 |
| CN | 106565406 A | 4/2017 |
| CN | 106607083 A | 5/2017 |
| WO | 2012057879 A1 | 5/2012 |

OTHER PUBLICATIONS

García-Trenco et al., Study of the interaction between components in hybrid CuZnAl/HZSM-5 catalysts and its impact in the syngas-to-DME reaction, Catalysis Today, Jul. 28, 2011, pp. 43 to 51, vol. 179, Elsevier B.V.
Office Action in priority application No. CN 201610931965.1, State Intellectual Property Office of the People's Republic of China, dated Apr. 18, 2019.
Second Office Action in priority application No. CN 201610931965.1, State Intellectual Property Office of the People's Republic of China, dated Sep. 4, 2019.
Xiao, Xingrong, "Supplementary Search, Application No. 2016109319651", Aug. 29, 2019, State Intellectual Property Office.
Xiao, Xingrong, "First Search, Application No. 2016109319651", Apr. 10, 2019, State Intellectual Property Office.

* cited by examiner

CATALYST FOR SYNTHESIZING AROMATIC HYDROCARBONS AND PREPARATION METHOD THEREFOR

PRIORITIES AND CROSS REFERENCES

This Application claims priority from International Application No. PCT/CN2017/098509 filed on 22 Aug. 2017 and Chinese Application No. 201610931965.1 filed on 24 Oct. 2016, the teachings of each of which are incorporated herein by reference in their entirety.

TECHNICAL FIELD

The present application refers to a catalyst for synthesizing aromatic hydrocarbons and preparation method thereof, and further refers to a method for synthesizing aromatic hydrocarbons using the catalyst.

BACKGROUND

Aromatic hydrocarbons, especially benzene, toluene and xylene, collectively known as BTX, are important organic chemical raw materials with a yield and scale second only to ethylene and propylene. The derivatives of aromatic hydrocarbons are widely used in fine chemical products and chemical products such as fuels, petrochemicals, chemical fiber, plastic and rubber.

At present, aromatic hydrocarbons are mainly produced from petroleum, wherein 70% of BTX aromatic hydrocarbons in the world come from a catalytic reforming process unit of a refinery. The catalytic reforming technology is a process using naphtha as a raw material, in which semi-regeneration and continuous regeneration reforming are adopted. Catalytic reforming generally adopts a platinum-containing catalyst. Typical processes for catalytic reforming are represented by UOP's CCR platformer process and IFP's Aromizer process. In addition, the production process of aromatic hydrocarbons based on petroleum route comprises gasoline hydrogenation technology, aromatic hydrocarbons extraction technology, heavy aromatic hydrocarbons lightening technology, and light hydrocarbon aromatization technology.

With the continuous development of society, the demand for aromatic hydrocarbons in the world is increasing. However, the increasingly shortage of petroleum resources cause the prices of aromatic hydrocarbons, especially BTX, to remain high. In view of the current energy structure of China's "rich coal and lean oil", it is of great significance to vigorously develop a coal chemical route to produce aromatic hydrocarbons. In the technology for producing aromatic hydrocarbons in coal chemical industry, the study on the technology of Methanol to Aromatics (MTA) using the methanol produced from the coal chemical platform is the most extensive. The technology for producing aromatic hydrocarbons from methanol generally adopts acidic ZSM-5 molecular sieve catalyst modified by metal zinc, gallium, silver, etc. However, the rapid decrease in the selectivity to aromatic hydrocarbons, the short life of catalyst, the low selectivity to BTX, and the significantly reduced performance of the catalyst after regeneration have constrained the large-scale industrial application of the technology for producing aromatic hydrocarbons from methanol. It is well known that industrial methanol is generally produced from syngas. If aromatic hydrocarbons are directly produced from syngas, the reaction path can be shortened, energy consumption can be saved, sewage discharge can be reduced, and fixed investment can be reduced. The study on the direct synthesis of aromatic hydrocarbons from syngas is less, the low selectivity to aromatic hydrocarbons, the poor stability of the catalyst and the inability of the deactivated catalyst to regenerate have restricted the further development of this technology.

Therefore, there is an urgent need for a catalyst with a high selectivity to aromatic hydrocarbons and stable performance.

SUMMARY OF THE INVENTION

According to the technical problems in the prior art, the present application has developed a catalyst with a high selectivity to aromatic hydrocarbons and stable performance. Moreover, the catalyst of the present application is particularly suitable for the one-step synthesis of aromatic hydrocarbons, thereby reducing the problem of a large amount of energy consumption due to the stepwise synthesis.

In particular, according to the first aspect of the present application, a catalyst comprising acidic molecular sieve particles and zinc-aluminum composite oxide particles is provided.

In a specific embodiment, other metal elements may be added into the zinc-aluminum composite oxide particles for modification by impregnation or without impregnation.

However, as a preferred embodiment, the zinc-aluminum composite oxide particles further comprise other metal elements.

As a more preferred embodiment, the other metal elements are metal elements other than zinc, aluminum, and radioactive elements.

As a further preferred embodiment, the other metal elements are at least one selected from a group consisting of zirconium, copper, platinum, palladium, and chromium.

In a specific embodiment, the mass ratio of the acidic molecular sieve particles to the zinc-aluminum composite oxide particles is in a range from 1:19 to 19:1.

In a preferred embodiment, the mass ratio of the acidic molecular sieve particles to the zinc-aluminum composite oxide particles is in a range from 4:1 to 1:4.

In a most preferred embodiment, the mass ratio of the acidic molecular sieve particles to the zinc-aluminum composite oxide particles is in a range from 2:1 to 1:2.

In a specific embodiment, the particle diameters of the acidic molecular sieve particles and the zinc-aluminum composite oxide are each independently less than or equal to 5 mm.

In a specific embodiment, the particle diameters of the acidic molecular sieve particles and the zinc-aluminum composite oxide are each independently less than or equal to 5 mm and greater than or equal to 0.1 mm.

In a preferred embodiment, the particle diameter of the acidic molecular sieve particles and the zinc-aluminum composite oxide particles are each independently less than or equal to 1 mm and greater than or equal to 0.1 mm.

In a more preferred embodiment, the particles have a particle diameter less than or equal to 0.5 mm and greater than or equal to 0.1 mm.

In a most preferred embodiment, the particles have a particle diameter less than or equal to 0.5 mm and greater than or equal to 0.25 mm.

In a specific embodiment, the acidic molecular sieve is an acidic molecular sieve having a pore framework with 10-membered and larger rings.

In a specific embodiment, the acidic molecular sieve comprises an acidic molecular sieve with at least one structure selected from a group consisting of MFI, BEA, FAU, EMT, MOR, FER, and MWW.

In a preferred embodiment, the acidic molecular sieve is an acidic molecular sieve with a MFI structure.

In a more preferred embodiment, the acidic molecular sieve is an acidic ZSM-5 molecular sieve.

In a most preferred embodiment, the acidic molecular sieve is an acidic ZSM-5 molecular sieve without being modified by a metal element.

In a specific embodiment, the atomic ratio of silicon to aluminum in the acidic ZSM-5 molecular sieve is Si/Al=3-200, preferably Si/Al=10-40.

In a specific embodiment, the acidic ZSM-5 molecular sieve may be subjected to or not subjected to post-treatment of desiliconization and/or post-treatment of dealumination.

In a specific embodiment, the post-treatment of desiliconization is an alkaline solution treatment. The commonly used alkaline solutions comprise aqueous solutions of sodium hydroxide, potassium hydroxide, ammonium hydroxide, sodium carbonate, and sodium hydrogencarbonate.

In a specific embodiment, the post-treatment of dealumination is an acid solution treatment or a steam treatment. The commonly used acid solutions comprise aqueous solutions of hydrochloric acid, nitric acid, oxalic acid, citric acid, and acetic acid. The temperature of conventional steam treatment is in a range from 400° C. to 700° C.

In a specific embodiment, the acidic ZSM-5 molecular sieve comprises one or more structure selected from a group consisting of a micron structure, a nanostructure, a microporous structure, and a mesoporous-microporous structure.

In a specific embodiment, the acidic ZSM-5 molecular sieve may not contain or contain one or more of metal elements comprising zinc, gallium, silver, copper, iron, molybdenum, lanthanum, cerium and the like.

In a specific embodiment, the acidic ZSM-5 molecular sieve contains a metal with a mass fraction of 0-10%.

In a specific embodiment, the metal in the acidic molecular sieve locates one or more at an ion exchange position of the molecular sieve, in a channel or on a surface of the acidic molecular sieve, and on a skeleton of the acidic molecular sieve.

In a specific embodiment, the metal is introduced into the acidic molecular sieve by one or more of in-situ synthesis, impregnation and ion exchange.

In a specific embodiment, the particle shape of the catalyst may be spherical, strip-shaped or clover-shaped, and may also be an irregular shape obtained by crushing and sieving large particles.

In a specific embodiment, the particles may be a powdered particles naturally formed without further molding during the preparation of the zinc-aluminum composite oxide and the acidic molecular sieve. Furthermore, the particle diameter of the powdered particles is less than or equal to 5 mm; preferably, the particle diameter of the powdered particles is less than or equal to 5 mm and greater than or equal to 0.1 mm; more preferably, the particles diameter of the powdered particles is less than or equal to 0.5 mm and greater than or equal to 0.1 mm; most preferably, the particles diameter of the powdered particles is less than or equal to 0.5 mm and greater than or equal to 0.25 mm.

The second aspect of the present application provides a method for preparing the catalyst described in the first aspect of the present application, comprising the following steps of:

1) a salt containing a zinc element and an aluminum element is formulated into an aqueous solution, and then the metal ions in the salt containing the zinc element and the aluminum element are coprecipitated by an aqueous solution of a precipitating agent to obtain a precipitate, and the precipitate is aged, washed, dried, and calcined to obtain the zinc-aluminum composite oxide particles;

2) the zinc-aluminum composite oxide particles are uniformly mixed with the acidic molecular sieve particles.

In a specific embodiment, the precipitating agent comprises at least one selected from a group consisting of sodium carbonate, potassium carbonate, ammonium carbonate, sodium hydrogencarbonate, potassium hydrogencarbonate, ammonium hydrogencarbonate, aqueous ammonia, sodium hydroxide, and potassium hydroxide.

In a specific embodiment, mixing is generally accomplished by mechanical agitation.

In a specific embodiment, conditions of precipitation in the step 1) are: temperature ranging from 60 to 80, and a pH of 6.0 to 8.0.

In a specific embodiment, calcination is carried out at a temperature of 400 to 600 for 1 hour to 4 hours in the step 1).

In a specific embodiment, the concentration of the zinc element in the aqueous solution in the step 1) is in a range from 0.1 mol/L to 2.0 mol/L; and the concentration of the aluminum element in the aqueous solution is in a range from 0.1 mol/L to 2.0 mol/L.

In a specific embodiment, further comprising a step 1-2) after the step 1) and before the step 2): placing the zinc-aluminum composite oxide particles in a salt solution in which other metal elements of zinc, aluminum and radioactive elements have been removed for modification.

In a specific embodiment, the other metal elements comprise at least one selected from a group consisting of zirconium, copper, platinum, palladium, and chromium in the step 1-2).

In a specific embodiment, the concentration of the single metal element of the other metal element in the aqueous solution is in a range from 0.1 mol/L to 2.0 mol/L in the step 1-2).

In a specific embodiment, in the step 1-2), the concentration of the zirconium element in the aqueous solution is in a range from 0.1 mol/L to 2.0 mol/L; and the concentration of the copper element in the aqueous solution is in a range from 0.1 mol/L to 2.0 mol/L; the concentration of platinum element in aqueous solution is in a range from 0.1 mol/L to 2.0 mol/L; the concentration of palladium element in the aqueous solution is in a range from 0.1 mol/L to 2.0 mol/L; the concentration of chromium element in the aqueous solution is in a range from 0.1 mol/L to 2.0 mol/L.

A third aspect of the present application provides a method for producing aromatic hydrocarbons, which comprises passing a raw material containing a syngas through a reactor loaded with catalyst and preparing the aromatic hydrocarbons under reaction conditions, wherein the catalyst is the catalyst described in the first aspect of the present application.

In a specific embodiment, the syngas comprises hydrogen and carbon monoxide.

In a preferred embodiment, the molar ratio of the hydrogen to the carbon monoxide in the syngas is in a range from 1:9 to 9:1.

In a more preferred embodiment, the molar ratio of the hydrogen to the carbon monoxide in the syngas is in a range from 1:3 to 3:1.

In an embodiment, the reaction is carried out at reaction conditions: a reaction temperature of 300 to 450, a reaction pressure of 0.5 MPa to 10.0 MPa, and a volumetric space velocity of 2000 $h^{-1}$ to 20000 $h^{-1}$ under standard gas conditions.

In a preferred embodiment, the reaction is carried out at a reaction conditions: a reaction temperature of 380 to 420, a reaction pressure of 3 MPa to 5 MPa, and a volumetric space velocity of 4000 $h^{-1}$ to 8000 $h^{-1}$ under standard gas conditions.

In the present application, the aromatic hydrocarbon refers to a hydrocarbon with a benzene ring structure in its molecule.

Preferably, in the present application, the aromatic hydrocarbon is at least one selected from the group consisting of benzene, toluene, ethylbenzene, methyl ethylbenzene, xylene, trimethylbenzene, and styrene.

In a specific embodiment, the aromatic hydrocarbon is one selected from a group consisting of benzene, toluene, and xylene.

In a preferred embodiment, the reactor is one or more fixed-bed reactors. A continuous reaction form can be used. The fixed-bed reactor may be one or more. When a plurality of fixed-bed reactors are employed, the reactors may be connected in series, in parallel, or in a form of a combination thereof.

In the present application, the concepts of "powder", "particle" and "powdered particles" is used interchangeable.

In the present application, normal atmospheric temperature means a temperature in a range from 20 to 30.

The beneficial effects that can be realized by the present application include:

1) The catalyst of the present application has a high selectivity to aromatic hydrocarbons, especially BTX, stable performance, and a long single-pass life.

2) The catalyst of the present application is particularly suitable for the one-step synthesis of aromatic hydrocarbons, thereby reducing the problem of a large amount of energy consumption by stepwise synthesis.

3) Comparing the method provided by the present application with the prior art, the deactivated catalyst has no significant degradation in performance after repeated regeneration.

DETAILED DESCRIPTION OF THE EMBODIMENTS

The application will be described in detail below with reference to examples, but the application is not limited to the examples.

The raw materials in the examples of the present application are all commercially purchased unless otherwise stated.

The analytical methods and the calculation methods for conversion rate and selectivity in the examples are as follows:

Automated analysis is performed using an Agilent 7890 gas chromatograph with a gas autosampler, a TCD detector connected to a TDX-1 packed column, and an FID detector connected to a FFAP capillary column.

In some embodiments of the application, both the conversion rate and the selectivity are calculated based on the number of moles of carbon:

The conversion rate of carbon monoxide=[(mole number of carbon in carbon monoxide in the feed)−(mole number of carbon in carbon monoxide in the discharge)]÷(mole number of carbon in carbon monoxide in the feed)×100%

The selectivity to aromatic hydrocarbons=(mole number of carbon in aromatic hydrocarbons in the discharge)÷(mole number of carbon in all hydrocarbon products in the discharge)×100%

The selectivity to BTX=(mole number of carbon in BTX in the discharge)÷(mole number of carbon in all hydrocarbon products in the discharge)×100%

The application is described in detail below by means of examples, but the application is not limited to the examples.

The Preparation of Catalyst

Example 1

The sodium type ZSM-5 (Catalyst Factory of Nankai University) with Si/Al=19 (atomic ratio) is exchanged with 0.8 mol/L aqueous ammonium nitrate solution at 80 for 3 times to obtain an ammonium type ZSM-5 molecular sieve. The ammonium type ZSM-5 molecular sieve is calcined at 550° C. for 4 hours in an air atmosphere, tabletted, crushed and then sieved to obtain acidic ZSM-5 molecular sieve particles of 0.25 mm-0.50 mm scale.

1 L nitrate solution mixed with 0.25 mol/L $Zn^{2+}$ and 0.50 mol/L $Al^{3+}$ is prepared. 0.5 mol/L sodium carbonate solution is added in the nitrate solution slowly, coprecipitation reaction temperature is controlled at 70° C., and pH value is kept at about 7.0 to coprecipitate metal ions and the coprecipitated metal ions are aged at this temperature for 2 hours, filtered, washed, dried, and calcined at 500° C. for 2 hours, tabletted, crushed and then sieved to obtain zinc-aluminum composite oxide ($ZnAlO_x$) particles of 0.25 mm-0.50 mm scale.

4 g of the above acidic ZSM-5 molecular sieve particles are uniformly mixed with 1 g of the above $ZnAlO_x$ particles to prepare a catalyst A.

Example 2

The sodium type ZSM-5 (Catalyst Factory of Nankai University) with Si/Al=19 (atomic ratio) is exchanged with 0.8 mol/L aqueous ammonium nitrate solution at 80 for 3 times to obtain an ammonium type ZSM-5 molecular sieve. The ammonium type ZSM-5 molecular sieve is calcined at 550° C. for 4 hours in an air atmosphere, tabletted, crushed and then sieved to obtain acidic ZSM-5 molecular sieve particles of 0.25 mm-0.50 mm scale.

1 L nitrate solution mixed with 0.25 mol/L $Zn^{2+}$ and 0.50 mol/L $Al^{3+}$ is prepared, 0.5 mol/L ammonium carbonate solution is added in the nitrate solution slowly, coprecipitation reaction temperature is controlled at 70° C., and pH value is kept at about 7.0 to coprecipitate metal ions and the coprecipitated metal ions are aged at this temperature for 2 hours, filtered, washed, dried, and calcined at 500° C. for 2 hours to obtain zinc-aluminum composite oxide powder. $Cr(NO_3)_3$ solution with a $Cr^{2+}$ concentration of 0.25 mol/L is used to impregnate the zinc-aluminum composite oxide powder at room temperature for 24 hours, followed by drying and calcining the zinc-aluminum composite oxide powder at 500° C. for 2 hours to obtain a modified zinc-aluminum composite oxide powder containing 5% chromium (5% Cr—$ZnAlO_x$). The 5% Cr—$ZnAlO_x$ powder is tabletted, crushed and sieved to obtain particles of 0.25 mm-0.50 mm scale.

4 g of the above acidic ZSM-5 molecular sieve particles are uniformly mixed with 1 g of the above 5% Cr—ZnAlO$_x$ particles to prepare a catalyst B.

Example 3

The sodium type ZSM-5 (Catalyst Factory of Nankai University) with Si/Al=19 (atomic ratio) is exchanged with 0.8 mol/L aqueous ammonium nitrate solution at 80 for 3 times to obtain an ammonium type ZSM-5 molecular sieve. The ammonium type ZSM-5 molecular sieve is calcined at 550° C. for 4 hours in an air atmosphere, tabletted, crushed and then sieved to obtain acidic ZSM-5 molecular sieve particles of 0.25 mm-0.50 mm scale.

1 L nitrate solution mixed with 0.1 mol/L Zn$^{2+}$ and 2.0 mol/L Al$^{3+}$ is prepared, 0.5 mol/L sodium carbonate solution is added in the nitrate solution slowly, coprecipitation reaction temperature is controlled at 70° C., and pH value is kept at about 7.0 to coprecipitate metal ions and the coprecipitated metal ions are aged at this temperature for 2 hours, filtered, washed, dried, and calcined at 500° C. for 2 hours to obtain Zn—Al composite oxide powder. Cu(NO$_3$)$_2$ solution with a Cu$^{2+}$ concentration of 0.4 mol/L is used to impregnate the zinc-aluminum composite oxide powder at room temperature for 24 hours, followed by drying and calcining the zinc-aluminum composite oxide powder at 500° C. for 2 hours to obtain a modified zinc-aluminum composite oxidepowder containing 7% copper (7% Cu—ZnAlO$_x$). The 7% Cu—ZnAlO$_x$ powder is tabletted, crushed and sieved to obtain particles of 0.25 mm-0.50 mm scale.

4 g of the above acidic ZSM-5 molecular sieve particles are uniformly mixed with 1 g of the above 7% Cu—ZnAlO$_x$ particles to prepare a catalyst C.

Example 4

The sodium type ZSM-5 (Catalyst Factory of Nankai University) with Si/Al=19 (atomic ratio) is exchanged with 0.8 mol/L aqueous ammonium nitrate solution at 80 for 3 times to obtain an ammonium type ZSM-5 molecular sieve. The ammonium type ZSM-5 molecular sieve is calcined at 550° C. for 4 hours in an air atmosphere, tabletted, crushed and then sieved to obtain acidic ZSM-5 molecular sieve particles of 0.25 mm-0.50 mm scale.

1 L nitrate solution mixed with 2.0 mol/L Zn$^{2+}$ and 0.1 mol/L Al$^{3+}$ is prepared, 0.5 mol/L sodium carbonate solution is added in the nitrate solution slowly, coprecipitation reaction temperature is controlled at 70° C., and pH value is kept at about 7.0 to coprecipitate metal ions and the coprecipitated metal ions are aged at this temperature for 2 hours, filtered, washed, dried, and calcined at 500° C. for 2 hours to obtain zinc-aluminum composite oxide powder. A mixed solution of Cr(NO$_3$)$_3$ solution with a Cr$^{2+}$ concentration of 0.1 mol/L and Zr(NO$_3$)$_4$ solution with a Zr$^{4+}$ concentration of 0.2 mol/L is used to impregnate the zinc-aluminum composite oxide powder at room temperature for 24 hours, followed by drying and calcining the zinc-aluminum composite oxide powder at 500° C. for 2 hours to obtain a modified zinc-aluminum composite oxide powder containing 2% chromium and 4% zirconium (2% Cr—4% Zr—ZnAlO$_x$). The 2% Cr—4% Zr—ZnAlO$_x$ powder is tabletted, crushed and sieved to obtain particles of 0.25 mm-0.50 mm scale.

4 g of the above acidic ZSM-5 molecular sieve particles are mixed with 1 g of the above 3% Cr—4% Zr—ZnAlO$_x$ particles uniformly to prepare a catalyst D.

Example 5

The sodium type ZSM-5 (Catalyst Factory of Nankai University) with Si/Al=19 (atomic ratio) is exchanged with 0.8 mol/L aqueous ammonium nitrate solution at 80 for 3 times to obtain an ammonium type ZSM-5 molecular sieve. The ammonium type ZSM-5 molecular sieve is calcined at 550° C. for 4 hours in an air atmosphere, tabletted, crushed and then sieved to obtain acidic ZSM-5 molecular sieve particles of 0.25 mm-0.50 mm scale.

1 L nitrate solution mixed with 0.1 mol/L Zn$^{2+}$ and 0.50 mol/L Al$^{3+}$ is prepared, 0.5 mol/L sodium carbonate solution is added in the nitrate solution slowly, coprecipitation reaction temperature is controlled at 70° C., and pH value is kept at about 7.0 to coprecipitate metal ions and the coprecipitated metal ions are aged at this temperature for 2 hours, filtered, washed, dried, and calcined at 500° C. for 2 hours to obtain zinc-aluminum composite oxide powder. A mixed solution of Pd(NO$_3$)$_3$ solution with a Pd$^{2+}$ concentration of 0.1 mol/L and Zr(NO$_3$)$_4$ solution with a Zr$^{4+}$ concentration of 0.2 mol/L is used to impregnate the zinc-aluminum composite oxide powder at room temperature for 24 hours, followed by drying and calcining the zinc-aluminum composite oxide powder at 500° C. for 2 hours to obtain a modified zinc-aluminum composite oxide powder containing 3% palladium and 4% zirconium (3% Pd—4% Zr—ZnAlO$_x$). The 3% Pd—4% Zr—ZnAlO$_x$ powder is tabletted, crushed and sieved to obtain particles of 0.25 mm-0.50 mm scale.

4 g of the above acidic ZSM-5 molecular sieve particles are uniformly mixed with 1 g of the above 3% Pd—4% Zr—ZnAlO$_x$ particles to prepare a catalyst E.

Example 6

The sodium type ZSM-5 (Catalyst Factory of Nankai University) with Si/Al=19 (atomic ratio) is exchanged with 0.8 mol/L aqueous ammonium nitrate solution at 80 for 3 times to obtain an ammonium type ZSM-5 molecular sieve. The ammonium type ZSM-5 molecular sieve is calcined at 550° C. for 4 hours in an air atmosphere to obtain an acidic ZSM-5 molecular sieve powder with a powder size of less than 0.1 mm.

1 L nitrate solution mixed with 0.25 mol/L Zn$^{2+}$ and 0.50 mol/L Al$^{3+}$ is prepared, 0.5 mol/L sodium carbonate solution is added in the nitrate solution slowly, coprecipitation reaction temperature is controlled at 70° C., and pH value is kept at about 7.0 to coprecipitate metal ions and the coprecipitated metal ions are aged at this temperature for 2 hours, filtered, washed, dried, and calcined at 500° C. for 2 hours to obtain a zinc-aluminum composite oxide (ZnAlO$_x$) powder with a powder size of less than 0.1 mm.

1 g of the above acidic ZSM-5 molecular sieve powder after calcination is uniformly mixed with 4 g of the above ZnAlO$_x$ powder, tabletted, crushed and then sieved to obtain a catalyst F of 0.25-0.50 mm scale.

Example 7

The sodium type ZSM-5 (AOKE company) with Si/Al=35 (atomic ratio) is exchanged with 0.8 mol/L aqueous ammonium nitrate solution at 80 for 3 times to obtain an ammonium type ZSM-5 molecular sieve. The ammonium type ZSM-5 molecular sieve is calcined at 550° C. for 4 hours in an air atmosphere, tabletted, crushed and then sieved to obtain acidic ZSM-5 molecular sieve particles of 0.25-0.50 mm scale.

1 L nitrate solution mixed with 0.25 mol/L $Zn^{2+}$ and 0.50 mol/L $Al^{3+}$ is prepared, 0.5 mol/L sodium carbonate solution is added in nitrate solution slowly, the coprecipitation reaction temperature is controlled at 70° C., and pH value is kept at about 7.0 to coprecipitate metal ions and the coprecipitated metal ions are aged at this temperature for 2 hours, filtered, washed, dried, and calcined at 500° C. for 2 hours, tableted, crushed and then sieved to obtain zinc-aluminum composite oxide ($ZnAlO_x$) particles of 0.25 mm-0.50 mm scale.

2.5 g of the above acidic ZSM-5 molecular sieve particles are uniformly mixed with 2.5 g of the above $ZnAlO_x$ particles to prepare a catalyst G.

Example 8

The sodium type ZSM-5 (Fuxutech company) with Si/Al=40 (atomic ratio) is exchanged with 0.8 mol/L aqueous ammonium nitrate solution at 80 for 3 times to obtain an ammonium type ZSM-5 molecular sieve. The ammonium type ZSM-5 molecular sieve is calcined at 550° C. for 4 hours in an air atmosphere, tabletted, crushed and then sieved to obtain acidic ZSM-5 molecular sieve particles of 0.25-0.50 mm scale.

1 L nitrate solution mixed with 0.25 mol/L $Zn^{2+}$ and 0.50 mol/L $Al^{3+}$ is prepared, 0.5 mol/L sodium carbonate solution is added in the nitrate solution slowly, coprecipitation reaction temperature is controlled at 70° C., and pH value is kept at about 7.0 to coprecipitate metal ions and the coprecipitated metal ions are aged at this temperature for 2 hours, filtered, washed, dried, and calcined at 500° C. for 2 hours, tableted, crushed and then sieved to obtain zinc-aluminum composite oxide ($ZnAlO_x$) particles of 0.25 mm-0.50 mm scale.

4 g of the above acidic ZSM-5 molecular sieve particles are uniformly mixed with 1 g of the above $ZnAlO_x$ particles to prepare a catalyst H.

Example 9

1 g of the acidic ZSM-5 molecular sieve particles prepared in Example 1 is uniformly mixed with 19 g of the $ZnAlO_x$ particles prepared in Example 1, to prepare a catalyst I.

Example 10

19 g of the acidic ZSM-5 molecular sieve particles prepared in Example 1 is uniformly mixed with 1 g of the $ZnAlO_x$ particles prepared in Example 1 to prepare a catalyst J.

Example 11

The particle diameters of the acidic ZSM-5 molecular sieve particles in Example 1 are prepared into 4.5 mm to 5 mm, and the particle diameters of the $ZnAlO_x$ particles in Example 1 are prepared into 4.5 mm to 5 mm. Other conditions are the same as that of Example 1. A catalyst K is prepared.

Example 12

The particle diameters of the acidic ZSM-5 molecular sieve particles in Example 1 are prepared into 0.8 mm to 1 mm, and the particle diameters of the $ZnAlO_x$ particles in Example 1 are prepared into 0.8 mm to 1 mm. Other conditions are the same as that of Example 1. A catalyst L is prepared.

Example 13

The particle diameters of the acidic ZSM-5 molecular sieve particles in Example 1 are prepared into 0.1 mm to 0.2 mm, and the particle diameters of the $ZnAlO_x$ particles in Example 1 are prepared into 0.1 mm to 0.2 mm. Other conditions are the same as that of Example 1. A catalyst M is prepared.

Performance Test of Catalyst

Example 14

5 g Catalyst A is placed in a stainless steel reaction tube with an inner diameter of 8 mm and activated with 50 ml/min of hydrogen at 300 for 4 hours, and the reaction is carried out under the following conditions: reaction temperature (T)=400, reaction pressure (P)=4.0 MPa, volumetric space velocity (GHSV)=5000 $h^{-1}$ under standard conditions, volume fraction of hydrogen in syngas (a mixed gas of CO and $H_2$) $V(H_2)$%=50%. After reacting for 500 hours, the product is analyzed by gas chromatography, and the results are shown in Table 1.

Examples 15-26

The reaction conditions and reaction results are shown in Table 1. The other operations are the same as those in Example 14.

TABLE 1

| | | Catalytic reaction results in Examples 14-26 | | | |
|---|---|---|---|---|---|
| Examples | Catalyst | Reaction conditions | The conversion rate of carbon monoxide (%) | The selectivity to aromatic hydrocarbon (%) | The selectivity to BTX (%) |
| 14 | A | T = 400; P = 4.0 MPa; GHSV = 5000 $h^{-1}$; $V(H_2)$ % = 50% | 30.5 | 80.3 | 75.2 |
| 15 | B | T = 380; P = 10.0 MPa; GHSV = 20000 $h^{-1}$; $V(H_2)$ % = 90% | 75.1 | 77.3 | 68.9 |
| 16 | C | T = 300; P = 0.5 MPa; GHSV = 2000 $h^{-1}$; $V(H_2)$ % = 10% | 12.4 | 82.1 | 79.6 |
| 17 | D | T = 450; P = 3.0 MPa; GHSV = 8000 $h^{-1}$; $V(H_2)$ % = 75% | 50.4 | 74.6 | 70.0 |
| 18 | E | T = 390; P = 5.0 MPa; GHSV = 6000 $h^{-1}$; $V(H_2)$ % = 40% | 25.9 | 83.9 | 70.8 |
| 19 | F | T = 340; P = 7.0 MPa; GHSV = 12000 $h^{-1}$; $V(H_2)$ % = 60% | 30.9 | 74.9 | 66.9 |

TABLE 1-continued

Catalytic reaction results in Examples 14-26

| Examples | Catalyst | Reaction conditions | The conversion rate of carbon monoxide (%) | The selectivity to aromatic hydrocarbon (%) | The selectivity to BTX (%) |
|---|---|---|---|---|---|
| 20 | G | T = 400; P = 4.0 MPa; GHSV = 5000 h$^{-1}$; V(H$_2$) % = 50% | 28.9 | 77.0 | 73.6 |
| 21 | H | T = 400; P = 4.0 MPa; GHSV = 5000 h$^{-1}$; V(H$_2$) % = 50% | 25.9 | 78.8 | 65.2 |
| 22 | I | T = 400; P = 4.0 MPa; GHSV = 5000 h$^{-1}$; V(H$_2$) % = 50% | 50.5 | 68.4 | 60.1 |
| 23 | J | T = 400; P = 4.0 MPa; GHSV = 5000 h$^{-1}$; V(H$_2$) % = 50% | 22.4 | 84.3 | 80.1 |
| 24 | K | T = 400; P = 4.0 MPa; GHSV = 5000 h$^{-1}$; V(H$_2$) % = 50% | 25.4 | 77.9 | 72.1 |
| 25 | L | T = 400; P = 4.0 MPa; GHSV = 5000 h$^{-1}$; V(H$_2$) % = 50% | 28.8 | 78.6 | 74.2 |
| 26 | M | T = 400; P = 4.0 MPa; GHSV = 5000 h$^{-1}$; V(H$_2$) % = 50% | 30.0 | 80.1 | 75.0 |

Regeneration Performance Test of Catalyst

Example 27

The catalyst deactivated in Example 14 is treated at 550 for 10 hours with a gas mixture comprising 2% oxygen and 98% nitrogen by volume fraction to regenerate the catalyst for one cycle and the reaction is carried out under the conditions of Example 14. Five cycles of regeneration is conducted in the same manner, and the catalytic activity data after 500 hours of each reaction is selected for comparison. The results are shown in Table 2.

TABLE 2

Catalytic reaction results in Example 27

| Times of regeneration | The conversion rate of carbon monoxide (%) | The selectivity to aromatic hydrocarbon (%) | The selectivity to BTX (%) | Life per cycle |
|---|---|---|---|---|
| 1 | 31.7 | 80.5 | 75.8 | 4000 |
| 2 | 30.8 | 81.3 | 74.9 | 4200 |
| 3 | 32.1 | 80.0 | 75.9 | 3900 |
| 4 | 31.0 | 79.6 | 74.8 | 3700 |
| 5 | 31.5 | 80.7 | 72.9 | 4100 |

The above is only a few embodiments of the present application, and is not intended to limit the present application. The preferred embodiments are shown as above, but are not intended to limit the present application. A slight change or modification of the technical content disclosed above made by the person skilled in art without departing from the technical solution of the present application is equivalent to the equivalent embodiment, and is within the scope of the technical solution.

The invention claimed is:

1. A catalyst, wherein the catalyst comprises a uniform mixture of acidic molecular sieve particles and coprecipitated zinc-aluminum composite oxide particles, and the zinc-aluminum composite oxide particles further comprise impregnated palladium oxide and zirconium oxide.

2. The catalyst according to claim 1, wherein a mass ratio of the acidic molecular sieve particles to the zinc-aluminum composite oxide particles is in a range from 1:19 to 19:1.

3. The catalyst according to claim 1, wherein the acidic molecular sieve particles and the zinc-aluminum composite oxide particles each independently have a diameter of less than or equal to 5 mm.

4. The catalyst according to claim 1, wherein the acidic molecular sieve is an acidic molecular sieve selected from the group consisting of 10-membered ring molecular sieves and molecular sieves having greater than 10-membered rings.

5. The catalyst according to claim 1, wherein the acidic molecular sieve comprises an acidic molecular sieve with at least one structure selected from a group consisting of MFI, BEA, FAU, EMT, MOR, FER, and MWW.

6. The catalyst according to claim 2, wherein the acidic molecular sieve particles and the zinc-aluminum composite oxide particles each independently have a diameter of less than or equal to 5 mm.

7. The catalyst according to claim 2, wherein the acidic molecular sieve is an acidic molecular sieve selected from the group consisting of 10-membered ring molecular sieves and molecular sieves having greater than 10-membered rings.

8. The catalyst according to claim 3, wherein the acidic molecular sieve is an acidic molecular sieve selected from the group consisting of 10-membered ring molecular sieves and molecular sieves having greater than 10-membered rings.

9. The catalyst according to claim 1, wherein the acidic molecular sieve particles and the zinc-aluminum composite oxide particles each independently have a diameter of less than or equal to 1 mm and greater than or equal to 0.1 mm.

10. The catalyst according to claim 1, wherein, the acidic molecular sieve is an acidic ZSM-5 molecular sieve.

11. The catalyst according to claim 1, wherein, the acidic molecular sieve is an acidic ZSM-5 molecular sieve exchanged with NH4+ ions followed by air calcination resulting in the H+ acidic form of ZSM-5.

12. The catalyst according to claim 1, wherein the catalyst has been prepared by a method comprising
1) Formulating a salt containing metal ions from a zinc element and an aluminum element into an aqueous solution,
2) Coprecipitating the metal ions in the salt containing the zinc element and the aluminum element by an aqueous solution of a precipitating agent to obtain a precipitate,
3) Aging, washing, drying and calcining the precipitate to obtain the coprecipitated zinc-aluminum composite oxide particles, and impregnating the coprecipitated zinc-aluminum composite oxide particles with a mixed solution containing salt compounds of palladium and zirconium followed by drying and calcining to obtain the zinc-aluminum composite oxide particles comprising palladium oxide and zirconium oxide,
4) Uniformly mixing the zinc-aluminum composite oxide particles comprising palladium oxide and zirconium oxide with the acidic molecular sieve particles;

wherein the precipitating agent comprises at least one selected from a group consisting of sodium carbonate, potassium carbonate, ammonium carbonate, sodium hydrogencarbonate, potassium hydrogencarbonate, ammonium hydrogencarbonate, aqueous ammonia, sodium hydroxide, and potassium hydroxide.

\* \* \* \* \*